United States Patent [19]

Farwell

[11] Patent Number: 5,363,858
[45] Date of Patent: Nov. 15, 1994

[54] METHOD AND APPARATUS FOR MULTIFACETED ELECTROENCEPHALOGRAPHIC RESPONSE ANALYSIS (MERA)

[75] Inventor: Lawrence A. Farwell, Potomac, Md.

[73] Assignee: Francis Luca Conte, Swampscott, Mass.

[21] Appl. No.: 57,607

[22] Filed: May 5, 1993

Related U.S. Application Data

[63] Continuation-in-part of Ser. No. 16,215, Feb. 11, 1993.

[51] Int. Cl.$^5$ ............................................. A61B 5/04
[52] U.S. Cl. ................................. 128/731; 607/139; 128/639
[58] Field of Search ..................... 128/731, 732, 639; 607/139, 140

[56] References Cited

U.S. PATENT DOCUMENTS

| | | | |
|---|---|---|---|
| 4,926,969 | 5/1990 | Wright et al. | 128/731 |
| 4,932,416 | 7/1990 | Farwell | 128/731 |
| 4,941,477 | 7/1990 | Farwell | 128/731 |
| 4,949,726 | 8/1990 | Hartzell et al. | 128/731 |
| 5,113,870 | 5/1992 | Rosenfeld | 128/731 |
| 5,137,027 | 8/1992 | Rosenfeld | 128/731 |
| 5,170,780 | 12/1992 | Rosenfeld | 128/731 |

OTHER PUBLICATIONS

Farwell, L. A. (1992) The Brain-Wave Information Detection (BID) System: A New Paradigm for Psychophysiological Detection of Information. Doctoral Dissertation, University of Illinois at Urbana-Champaign, pp. Cover, iii–vii, 1–165 Jun., 1992.

Farwell, L. A. (1992) Two New Twists on the Truth Detector: Brain-Wave Detection of Occupational Information, Psychophysology 29: 4A: S3. p. 20 Sep. 1992.

Farwell, L. A. and Donchin, E. (1986). The Brain Detector: P300 in the Detection of Deception. Psychophysiology, 24: 434, page: Cover, 434 Jul. 1986.

Farwell, L. A. and Donchin, E. (1991). The Truth Will Out: Interrogative Polygraphy ("Lie Detection") with Event-Related Brain Potentials. Psychophysiology, 28, 5: 531–47. Sep. 1991.

(List continued on next page.)

Primary Examiner—William E. Kamm
Assistant Examiner—Scott M. Getzow
Attorney, Agent, or Firm—Francis L. Conte

[57] ABSTRACT

A method and apparatus for multifaceted electroencephalographic response analysis (MERA) is described. MERA involves presenting stimuli to a subject through at least one of the visual and auditory modalities, recording electrophysiological brain responses indicative of information processing in response to said stimuli, and analyzing multiple features of said brain responses. This technique is used both to detect concealed information in the brain and to communicate directly from a brain to a computer, and thus to command computers and also to command mechanical devices. The memory and encoding related multifaceted electroencephalographic response (MERMER), a particular brain response elicited by, and unfolding within two seconds of the onset of, noteworthy stimuli, involving an electrically positive aspect generally maximal parietally followed by an electrically negative aspect with substantial frontal amplitude, and also involving characteristic changes in the frequency domain, is detected, analyzed, and applied for the above stated purposes. The MERMER is elicited by stimuli that refer to concealed information noteworthy to an individual and also by stimuli that are noteworthy due to a subject's desire to communicate the information to which they refer. Responses are compared with at least one of a) responses to other stimuli known to be irrelevant, and b) responses to other stimuli known to be noteworthy, in order to determine the presence or absence of the MERMER in response to the stimuli in question. In this manner, concealed information is detected, and information of significance is communicated.

57 Claims, 3 Drawing Sheets

OTHER PUBLICATIONS

Farwell, L. A. and Donchin, E. (1988). Talking Off the Top of Your Head: Toward a Mental Prosthesis Utilizing Event-Related Brain Potentials. *Electroencephalography and Clinical Neurophysiology,* 70: 510–523. Apr. 1988.

Farwell, L. A., Martinerie, J. M., Bashore, T. H., Rapp, P. E., and Goddard, P. H. (1993). Optimal Digital Filters for Long-Latency Components of the Event-Related Brain Potential. *Psychophysiology,* 30, 306–315. May 1993.

Johnson, M. and Rosenfeld, J. P. (1992). Oddball—Evoked P300-Based Method of Deception Detection in the Laboratory II: Utilization of Non-Selective Activation of Relevant Knowledge, *International Journal of Psychophysiology* 12:289–306 Feb. 1992.

Rapp, P. E., Albano, A. M., Schmah, T. I., and Farwell, L. A., Filtered Noise Can Mimic Low-Dimensional Chaotic Attractors, *Physical Review E,* 47, 4: 2289–97. Apr. 1993.

Rosenfeld, J. P., Angell, A., Johnson, M., and Quan, J. (1991). An ERP-Based, Control-Question Lie Detector Analog: Algorithms for Discriminating Effects Within Individual's Average Waveforms. *Psychophysiology,* 28, 3: 319–335. May 1991.

Rosenfeld, J. P. and Kim, M. (1991). Ongoing Pain as a Mental Workload Indexed by P300 Depression: Discrimination of Real and Feigned Pain Conditions. *Psychophysiology* 28, 3: 336–343. May 1991.

Rosenfeld, J. P., Nasman, V. T., Whalen, R., Cantwell, B., and Mazzeri, L. (1987) Late Vertex Positivity in Event-Related Potentials as a Guilty Knowledge Indicator: A New Method of Lie Detection, *International Journal of Neuroscience,* 34: 125–129. Sep. 1987.

Sutter, E. (1983) An Oculo-Encephalographic Communication System, *Proc. 6th Annual Conf. of Rehabilitation Engineering,* 171–173. Sep., 1983.

Wasserman, S. and Bockenholt, U. (1989), Bootstrapping: Applications to *Psychopysiology, Psychophysiology* 26: 208–221. Mar. 1989.

Rosenfeld, J. P., Bhat, K., Miltenberger, A., and Johnson, M. (1992). Event-Related Potentials in the Dual-Task Paradigm: P300 Discriminates engaging and non-engaging films when film-viewing is the primary task. *International Journal of Psychophysiology,* 12:221–232, Nov., 1992.

Rosenfeld, J. P., Cantwell, B., Nasman, V. T., Wojdak, V., Ivanov, S., and Mazzeri, L. (1988). A Modified, Event-Related Potential-Based Guilty Knowledge Test, *International Journal of Neuroscience,* 42: 157–61. Oct. 1987.

METHOD AND APPARATUS FOR MULTIFACETED ELECTROENCEPHALOGRAPHIC RESPONSE ANALYSIS (MERA)

This is a continuation-in-part of application Ser. No. 08/016,215, filed Feb. 11, 1993, presently pending.

BACKGROUND

This invention relates to the detection and signal processing of electrical brain activity. The purposes of this invention include the detection of information processing undertaken in the brain, the detection of concealed information in the brain, communication from the brain to a computer, and command and control of computers and electronic and mechanical equipment by the brain.

The Farwell MERA System is a new technology for the detection of concealed information that revolves around the non-invasive recording of brain electrical activity. The electrical brain activity pattern recorded and of interest is a specific multifaceted electroencephalographic response (MER) that occurs immediately after an examinee is visually presented (via a computer screen) with words, short phrases, acronyms, or pictures that are recognized and cognitively processed by that subject. This phenomenon, coupled with its absence following the presentation of the same information to a subject for whom the material is unknown or irrelevant, is the basis for discriminating between subject guilt and innocence. This would potentially allow for the determination of a whole host of issues of interest to the law enforcement and intelligence communities, e.g., (1) does a suspect have guilty knowledge connecting him to specific investigated criminal activity, (2) does an intelligence source have knowledge of the internal workings of a hostile intelligence agency that would indicate that he was an intelligence officer of that agency and not who he claimed to be, (3) has an informant, a debriefed spy, or a suspected member of a criminal organization accurately described the entirety of his actions and knowledge, (4) did a convicted serial killer who claims to have killed 40 to 50 individuals, other than the one(s) he was convicted of, actually commit these acts, or are these claims merely the bravado of a condemned prisoner.

The potential benefit of this program extends to a broad range of law enforcement applications, including organized crime, violent crime, white-collar crime, drug-related crime, foreign counterintelligence, non-traditional targets, and other categories of casework as well. This new technology promises to be of tremendous benefit both at the national level and for state and local law enforcement agencies.

This application describes a technology that is capable of detecting concealed information stored in the brain through the electrophysiological manifestations of information-processing brain activity. Additional information is described in a previous patent application of the inventor, U.S. patent application Ser. No. 08/016,215, entitled "Method and Apparatus for Truth Detection" filed on Feb. 11, 1993, which is expressly incorporated here by reference.

This technique provides a means of distinguishing guilty and innocent individuals in a wide variety of law enforcement and information detection situations. The research described below demonstrates that the system is also effective in distinguishing between members of a particular organization (in this case, the FBI) and others who are not knowledgeable regarding that organization.

When a crime is committed, traces of the event are left at the scene of the crime and elsewhere. The task of the investigators is to reconstruct what has happened and who has been involved, based on the collection of such evidence.

In addition to the physical and circumstantial evidence that can be obtained, there is one place where an extensive record of the crime is stored: in the brain of the perpetrator. If this record could be tapped, criminal investigation and counterintelligence could be revolutionized.

Until recently, the only method of attempting to discern what information regarding a crime or other situation of interest was stored in the brain of a suspect or witness has been (1) to interrogate the subject, and (2) to attempt to determine whether or not the subject is lying.

Conventional control question (CQT) polygraphy has been used as an aid in the attempt to detect deception in such reports. The fundamental theory of conventional polygraphy is that a deceptive individual will be more concerned with and experience more emotional arousal in response to relevant questions than control questions, and this emotional arousal will be accompanied by corresponding physiological arousal which can be measured. Traditional interrogative polygraph ("lie detection") methods rely upon using questioning formats in conjunction with the recording of physiological parameters that reflect autonomic nervous system (ANS) activity (e.g. blood pressure, heart rate, sweating, etc.). This information is peripheral to the cognitive aspects of deception or of concealing guilty information.

Multifaceted electroencephalographic response analysis (MERA) technology focuses on the origins (at the level of subject recognition of guilty knowledge) of concealed information rather than the peripheral physiological manifestations of that knowledge. In addition to being a more direct physiological approach (central nervous system vs. peripheral) to the question at hand, the Farwell MERA System may well overcome certain difficulties inherent with standard polygraphy: (1) Innocent as well as guilty individuals may respond emotionally and physiologically to crime-relevant questions, which may result in an innocent subject falsely being found deceptive; (2) guilty individuals may fail to respond in the expected way either emotionally or physiologically; (3) certain mental and physical countermeasures can be practiced successfully with standard technology; and (4) a conventional polygraph exam is highly stressful for the examinee, and involves deception by the polygrapher.

In a conventional polygraph test, emotion-driven physiological responses to relevant questions (regarding the situation under investigation) are compared to responses to control questions, which are invasive, personal questions not relevant to the issue at hand that are designed to be emotionally and physiologically disturbing to the subject. A greater response to the relevant questions leads to a deceptive ("guilty") determination; a greater response to the control questions leads to a non-deceptive ("innocent") determination. In an attempt to avoid a false positive result (non-deceptive subject falsely found deceptive), the examiner must ask penetrating questions in the pre-test interview to find personal material sufficiently disturbing and stress-producing to produce effective control questions. To elicit a stress response to the control questions during the test, the examiner typically deceives the subject, leading him to believe that a large response to control questions will make him appear guilty (deceptive), rather than innocent (non-deceptive). This deception by the examiner is necessary, or at least highly instrumental, to produce the response. Thus, in conventional polygraphy, innocent subjects—even if they are correctly determined to be innocent and truthful—are deceived and subjected to a highly invasive and stressful situation both during the pre-test interview and during the test.

This latter shortcoming is generally justified by the correct end result of finding an innocent subject non-deceptive to the relevant questions, but could be avoided altogether with MERA technology, which depends entirely on information processing brain activity (i.e., recognition and processing of significant information) rather than an artful and disturbing manipulation designed to produce emotional and physiological responses to control question material. In fact, the pre-test interview for a MERA-based exam is a very clinical, emotionally neutral experience for both guilty and innocent subjects. The in-test portion of the MERA-based exam does not involve the asking of any questions, only the non-invasive recording of brain electrical activity as a subject views verbal or pictorial information on a computer screen.

A new study conducted by the inventor in collaboration with SSA Drew C. Richardson, Ph.D., FSRTC, FBI Laboratory, described below, has shown the Farwell MERA System to be capable of detecting whether or not an individual has participated in FBI new agent training at the Academy. New FBI agents in training at the FBI Academy at Quantico were correctly identified as such, and individuals unfamiliar with the FBI were also correctly classified. The application of this technique in foreign counterintelligence is obvious: if this technology can be utilized to detect an FBI agent, it can also be used to detect agents of other organizations, including both intelligence organizations and international criminal organizations. The detection of information stored in the brain is indeed central to the investigation of all types of crimes—e.g., organized crime, violent crime, white-collar crime, drug-related crime, industrial espionage, non-traditional targets—as well as foreign counterintelligence operations.

Although several previous experiments, including those reported in the above cited United States patent application incorporated here by reference, used an experimental design that included some of the major features specified herein, the MERA technique was not practiced in the prior art, the MERMER was not detected and characterized in previous experiments, and the MERMER was not used in the analysis procedures implemented to detect which information was noteworthy for the subject. For this reason, all other previous methods lacked a critical and central feature in the effectiveness of the present invention.

There are several reasons why the MERMER was not detected in previous experiments. Previous experiments were structured so as to detect only the well-known P3b or P300, and failed to detect the MERMER (e.g., the following references cited in the above cited U.S. patent application included herein by reference: Farwell and Donchin, 1986; 1991; Rosenfeld et al., 1987, 1991; see also Farwell, U.S. Pat. No. 4,941,477; Rosenfeld, J. P., Cantwell, B., Nasman, V. T., Wojdac, V., Ivanov, S. and Mazzeri, L., A modified, event-related potential-based guilty knowledge test, *International Journal of Neuroscience*, 1988, 42, 157–161; Rosenfeld, U.S. Pat. No. 4,932,416). These and all other previous experiments failed to detect the frontally prominent, late negative facet of the MERMER and the frequency domain changes that characterize a MERMER. There are several reasons for this:

(A) Time domain responses (event-related potentials)

(1) The P300 or P3b, the response sought in previous experiments, is maximal at the parietal scalp location, and the negative facet of the MERMER has a considerably different scalp distribution, particularly when difference waveforms are taken into account. Previous experiments focused on the parietal, or in some cases central, scalp locations, and thus did not detect or did not accurately characterize the late, frontally prominent, negative potential that characterizes a MERMER.

(2) The frontally-prominent, negative facet of the MERMER does not begin until about one second after the stimulus, and does not peak until up to 1600 msec after the stimulus. Earlier experiments analyzed only a limited time epoch, and thus this negative component was not accurately or fully represented in the data analyzed.

(3) In some previous experiments, the inter-stimulus interval was only about 1500 msec, and/or the data collection epoch was only a little over one second. Such an interval is insufficient for the frontally prominent, negative component of the MERMER to develop fully.

In order to characterize the time-domain facets of the MERMER accurately, and to extract the full complement of data it provides in the time domain, it is necessary to analyze the frontal as well as parietal and central data, for 1.8 to 2 seconds after the stimulus. Farwell and Donchin (1991) did analyze frontal data, but their analysis epoch ended 1200 msec after the stimulus onset, and the inter-stimulus interval was only 1550 msec: both of these are too short to allow for the occurrence or detection of the negative component. Thus, Farwell and Donchin concluded that the frontal scalp location did not contribute to the critical discrimination between brain responses. Rosenfeld et al. (1991) observed some late negativity at the parietal scalp location in a similar experimental design, but did not analyze the data from the frontal site in making their discriminations between brain responses to different types of trials, and did not identify or report the frontal-negative aspect of the MERMER (they did collect frontal data). None of the above researchers recognized or described the MERMER as a phenomenon.

(B) Frequency domain (1) All similar previous experiments analyzed the data only in the time domain. The frequency-domain changes that characterize a MERMER can not, of course, be detected in the time domain.

(2) All similar previous experiments involving detection of concealed information or brain-to-computer communication used signal averaging as a means of noise reduction, and applied their detection methods to averaged signals. Although the alternating-current, frequency-domain signals change in response to the stimulus, these signals are not phase-locked to the stimulus, and therefore the frequency-domain changes are eliminated by signal averaging.

(3) Previous research on frequency-domain changes (e.g., on alpha blocking), all differ from the present invention in that they did not use similar stimulus presentation designs, did not detect specific or concealed information, did not communicate specific information in the manner accomplished by the present invention, did not simultaneously measure and process time-domain changes (in fact, the analog filters used in previous research for frequency domain data markedly attenuate or virtually eliminate the very slow activity in the range of 0.1 to 2 Hz that contributes to the MERMER) did not process time frequency data, and did not use the signal processing methods (e.g., bootstrapping correlation) described herein.

In addition to the references cited in the above cited United States patent application incorporated here by reference, the inventor published research on the psychophysiological detection of concealed information in the following scientific publications. None of the material constituting the inventions claimed herein was presented.

1) Farwell, L. A. (1992a) The Brain-wave Information Detection (BID) System: A New Paradigm for Psychophysiological Detection of Information. Doctoral Dissertation, University of Illinois at Urbana-Champaign.

2) Farwell, L. A. (1992b) Two New Twists on the Truth Detector: Brain-wave Detection of Occupational Information. *Psychophysiology*, 29,4A:S3.

Numerous other systems have been developed to communicate with a computer. None have features that approximate the present system. Neither MERA nor the MERMER were used in previous systems.

Farwell and his colleagues developed a system based on the P3 component (described in the above cited United States patent application incorporated here by reference). That system, however, was unable to make use of the MERMER, because 1) the maximum interstimulus interval used was 600 msec, and a MERMER can take as long as 2000 msec to develop fully; 2) only the parietal scalp location was recorded. Thus the system failed to detect both the frontal negative facet and the frequency domain facets of the MERMER.

The task undertaken to elicit a MERMER is more cognitively complex, and more memory-intensive, than the tasks used to focus attention on the chosen item in previous attempts to use brain electrical activity to provide an interface with a computer. For example, Farwell and Donchin used a simple counting task (Farwell, L. A., and Donchin, E., Talking off the top of your head: toward a mental prosthesis utilizing event-related brain potentials, *Electroencephalography and Clinical Neurophysiology*, 1988, 70: 510–523). This could be expected to elicit a P300, but probably would not have been effective in eliciting a MERMER, even if they had recorded a long enough data epoch to detect a MERMER.

Dr. John Wolpaw of Stoneybrook and his colleagues (personal communication) have developed a system to move a cursor on a computer screen using feedback and analysis of electrical brain activity. This system is essentially a biofeedback system, and, unlike the present system, does not detect the information-processing activity involved in conscious choice and memory, nor has it been used to command a speech synthesizer, a robot, a computer function beyond simply moving the cursor on the screen, or any mechanical device.

Sutter (Sutter, E. E., An oculo-encephalographic communication system. In: *Proceedings of the 6th Annual Conference of Rehabilitation Engineering*, San Diego, 1983: 171–173.) developed a system to use visual sensory evoked potentials to convey to a computer where a subject's eyes are pointed, wherein the subject conveys his choice by engaging in the motor activity of pointing the eyes to a certain location, and subsequent sensory evoked potentials elicited by a flashing light at the particular location are detected to convey to the computer where the eyes are pointed. That system, of course, has nothing to do with detecting the brain responses that reflect the cognitive, information-processing activities that are involved in making the conscious choices detected by the present system. Unlike the present system, the choices are followed by a motor activity (moving the eyes to a particular location), and detected on the basis of sensory activity (responses to a flashing light at the location); the detection of cognitive, information-processing activity related to choice, stimulus significance, and memory is lacking.

None of the above publications disclose the innovations that constitute the invention claimed herein.

SUMMARY

The detection of concealed information stored in the brain of suspects, witnesses, intelligence sources, and others is of central concern to all phases of law enforcement and intelligence operations. The Farwell MERA System for multifaceted electroencephalographic response analysis (MERA) presents a new paradigm in the psychophysiological detection of concealed information. This new system detects information directly, on the basis of the electrophysiological manifestations of information-processing brain activity, measured noninvasively from the scalp. Since the Farwell MERA System depends only on brain information processing, it does not depend on the emotional response of the subject.

The Farwell MERA System utilizes multifaceted electroencephalographic response analysis (MERA) to detect information stored in the human brain. A memory and encoding related multifaceted electroencephalographic response (MERMER) is elicited when an individual recognizes and processes an incoming stimulus that is significant or noteworthy. When an irrelevant stimulus is seen, the MERMER is absent. This pattern occurs within less than a second after the stimulus presentation, and can be readily detected using EEG amplifiers and a computerized signal-detection method.

The Farwell MERA System incorporates the following procedure. A sequence of words, phrases, or pictures is presented on a video monitor under computer control. Each stimulus appears for a fraction of a second. Three types of stimuli are presented: "targets," "irrelevants," and "probes." The targets are made relevant and noteworthy to all subjects: the subject is given a list of the target stimuli and instructed to press a particular button in response to targets and another button in response to all other stimuli. Since the targets are noteworthy for the subject, they elicit a MERMER. Most of the non-target stimuli are irrelevant, having no relation to the situation under investigation. These irrelevants do not elicit a MERMER. Some of the non-target stimuli are relevant to the situation under investigation. These relevant stimuli are referred to as probes.

For a guilty subject, the probes are noteworthy due to the subject's knowledge of that situation, and therefore probes elicit a MERMER when the subject is guilty (or "knowledgeable"). Probes are indistinguishable from the irrelevants for an innocent subject, and thus probes do not elicit a MERMER if the subject is innocent.

The Farwell MERA System is advantageously computer controlled, including presentation of the stimuli and recording of electrical brain activity, as well as a brain response signal processing method that compares the responses to the three types of stimuli and produces a determination of "innocent" or "guilty," and a statistical confidence level for this determination.

An apparatus for recording the electrical brain activity includes a headband with disposable electrodes that can be individually positioned.

The Farwell MERA System is expected to have potential application in a wide range of law enforcement and intelligence operations, from detecting whether a suspect has knowledge that would identify him as the perpetrator of a crime to detecting whether an individual has knowledge that would indicate that he had undergone training by a foreign intelligence organization.

A related embodiment is the Farwell MERA Brain Communicator. In this system, stimuli are presented to a subject representing different options from among which the subject makes conscious choices. The brain responses are analyzed to detect the choice eliciting a MERMER, indicating that this choice is particularly noteworthy for the subject and is therefore the option that the subject wishes to communicate. In this manner, a subject can command and control not only a computer but also other electronic and mechanical devices using electrical brain activity.

DETAILED DESCRIPTION

The Farwell MERA System

Figure 1:
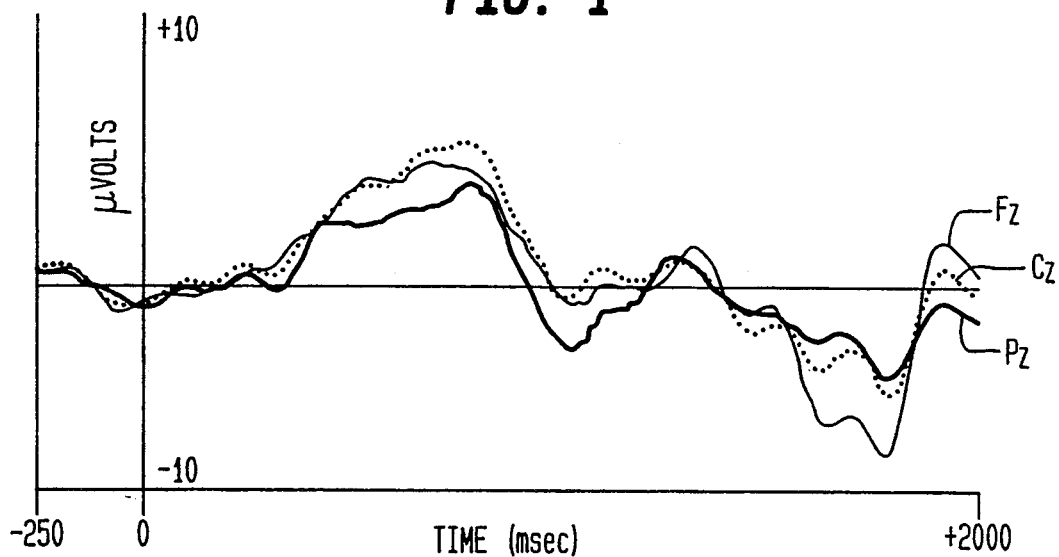
FIG. 1 is a plot of normalized responses to FBI-relevant stimuli from a subject knowledgeable about the FBI, containing a MERMER revealing this concealed knowledge (a "guilty" determination).

In the application of the Farwell MERA System, brain responses to certain types of stimuli are analyzed to detect a specific multifaceted electroencephalographic response (MER) known as the memory and encoding related multifaceted electroencephalographic response (MERMER). The MERMER contains several facets, both in the time and frequency domains, that can be detected with sophisticated signal processing procedures. It is elicited by stimuli that are noteworthy to a subject.

In the preferred embodiment, the Farwell MERA System presents visual stimuli consisting of short phrases on a video screen under computer control. Three categories of stimuli are presented: "probes," "targets," and "irrelevants."

Probes are stimuli relevant to a situation, such as a crime under investigation. Irrelevants are, as the name implies, irrelevant. For each probe stimulus, there are approximately four irrelevant stimuli. The stimuli are structured such that the probes and irrelevants are indistinguishable for an innocent subject. That is, if a given probe is an article of clothing relevant to the crime, four articles of clothing irrelevant to the crime are also presented; if a particular probe stimulus is a name, there are four irrelevant stimuli that are also names, and so on.

In addition to the probes and the irrelevants, a third type of stimuli, designated as targets, is presented. About one-sixth of the stimuli are targets, one for each probe. The subject is given a list of the targets, and is required to press a particular button whenever a target is presented. (For all other stimuli, the subject is instructed to press another button.) Each target is the same type of item as one of the probes and the several corresponding irrelevants. The targets, since they are recognized and require a particular response, are noteworthy for all subjects. The irrelevants are not noteworthy for any subjects. The probes are noteworthy only to the subjects who possess the knowledge necessary to recognize them—that is, the knowledge specific to the situation under investigation.

The inventor has discovered that brain information processing of noteworthy stimuli results in a characteristic brain electrical response known as a memory and encoding related multifaceted electroencephalographic response (MERMER). One of the most easily measured aspects of this response (and the only one measured in early research) is an electrically positive component, maximal at the midline parietal area of the head, with a peak latency of approximately 300 to 800 msec. It is referred to variously as P300, P3, P3b, or late positive component (LPC). Another important aspect of the MERMER is an electrically negative component, prominent at the midline frontal area, with an onset latency of approximately 800 to 1200 msec. These components can be readily recognized through signal averaging procedures. A third aspect of the MERMER is a pattern of changes in the frequency domain characterized by a phasic shift in the frequency power spectrum that can be detected using single-trial signal processing techniques.

An innocent subject recognizes only two types of stimuli: relevant, noteworthy, rare targets and irrelevant, frequent stimuli (consisting in fact of true irrelevants, plus probes—which he does not distinguish as being different from the irrelevants). The targets elicit a MERMER, and the irrelevants and (unrecognized) probes do not. A guilty subject, however, recognizes a second noteworthy type of stimuli, namely the probes, which are relevant to a crime or other situation in which he has participated. Thus, for a guilty subject, the probes, too, elicit a MERMER.

What this experimental design accomplishes, essentially, is to create a two-stimulus series for an innocent individual, and a three-stimulus series (with the same stimuli) for a guilty individual. The targets provide a template for a response to stimuli known to be particularly noteworthy— MERMER-producing stimuli. The irrelevants provide a template for a response to stimuli that are irrelevant—non-MERMER-producing stimuli.

The determination of guilt or innocence consists of comparing the probe responses to the target responses, which contain a MERMER, and to the irrelevant responses, which do not. If the probe responses are similar to the target responses, one can conclude that the subject recognizes the probes—which only someone knowledgeable about the crime would do—and therefore is "guilty" (or, more correctly, "knowledgeable"). If the brain responses to the probes are like those to the irrelevants—i.e., lacking a MERMER—then the subject can be determined to be "innocent." (Note that what is detected is not actually guilt or innocence, but knowledge or lack of knowledge regarding the situation under investigation. In order for this to be an effective indicator of guilt or innocence, stimuli must be structured such that only a guilty person would recognize the probe stimuli.) The statistical technique of bootstrapping is employed to compare the brain responses to the different types of stimuli, to make a determination of "innocent" or "guilty," and to provide a statistical confidence for this determination.

Figure 6:
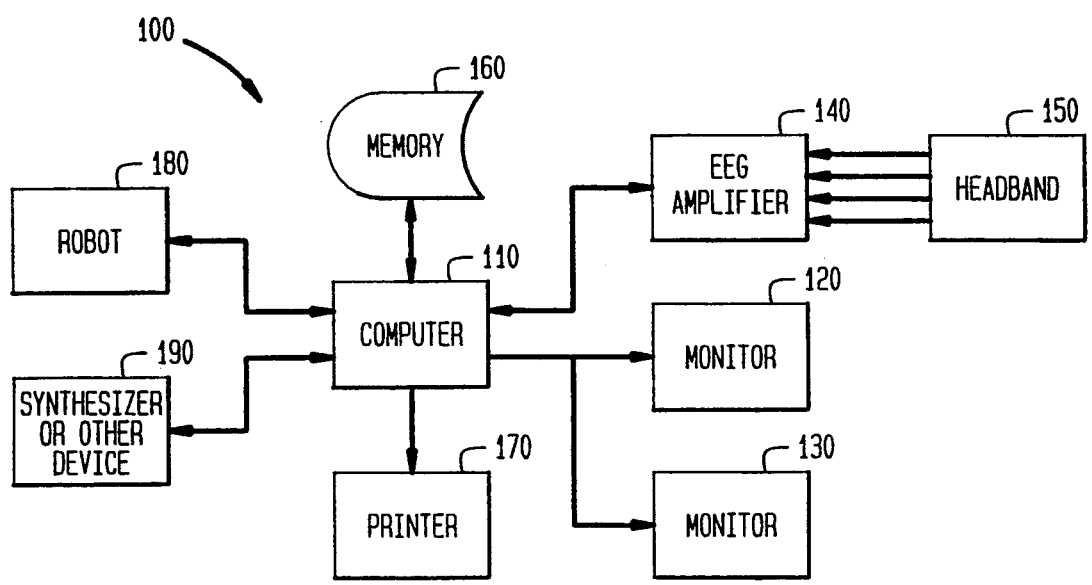
FIG. 6 is a block diagram of an apparatus in accordance with applicant's invention.

Referring to FIG. 6, the Farwell MERA System 100 comprises a personal computer 110 (e.g., 486-66 MHz Gateway 2000), a data acquisition board (e.g., Scientific Solutions Lab Master AD), a graphics card for driving two monitors 120, 130 from one PC (e.g., Colorgraphics Super Dual VGA), a four-channel EEG amplifier system 140 (e.g., Neuroscience), and software for data acquisition and signal processing. The electrodes used to measure electrical brain activity are held in place by a special headband 150 designed and constructed by the inventor for this purpose. This new means for attaching electrodes is more convenient and comfortable for the subject as well as quicker and easier for the operator than previously available means. The software presents the stimuli, collects the electroencephalographic data, and analyzes the data.

Stimulus duration of the visual stimuli, e.g., a scene or a word, presented on a computer screen is relatively brief, e.g., 300 msec , and interstimulus interval is about 2 seconds from the onset of one stimulus to the next stimulus onset.

Brain electrical activity is recorded from three midline scalp locations on the head: frontal (Fz), central (Cz) and parietal (Pz), referenced to linked mastoids (behind the ear). It will be understood that additional brain signals measured from other scalp locations may be used as well. Eye movement generated electrical activity is recorded by electrodes above and below one eye.

Brain electrical activity is amplified, analog filtered (e.g., low-pass 30 Hz, high pass 0.1 Hz) digitized at 256 Hz, analyzed on-line, and stored on tape or disk 160. Each trial consists of the brain activity recorded in conjunction with one stimulus presentation, about 2 seconds of data.

The full set of stimuli, consisting of the three stimulus types described above, is randomized, and the stimuli are presented to the subject one at a time on the video monitor 120. Typically, there are about 6 probes, 6 targets, and 24 irrelevants. Once all of the stimuli have been presented, they are randomized again and presented again. This is repeated until a specified number of trials have been presented, or until a sufficient number of artifactfree trials have accumulated. The required number of artifact-free trials may be for the total and/or for the number of trials of one or more of the 3 types.

A primary innovation of the present application is the detection of concealed information stored in the human brain based on the measurement of a newly discovered brain response known as a MERMER (memory and encoding related multifaceted electroencephalographic response). Three facets of the MERMER have been measured. Two of these facets are new discoveries of the inventor, and have not been reported prior to the research that forms the foundation for this application. The third facet is a component that was fundamental to the prior art and to the above cited United States patent application incorporated here by reference. The two newly discovered facets of the MERMER are as follows: 1) an electrically negative component, maximal at the midline frontal area, with a peak latency of approximately 1400 to 1600 msec; and 2) a pattern of changes in the frequency domain characterized by a phasic shift in the frequency power spectrum that can be detected using single-trial signal processing techniques.

A third facet of the MERMER is an electrically positive component, maximal at the midline parietal area of the head, with a peak latency of approximately 300 to 800 msec. It is referred to variously as P300, P3, P3b, or late positive component (LPC). This component alone formed the basis of the prior art.

The scalp distribution of the MERMER is complex, and changes during the course of the response. In order to reflect accurately the functional significance of the MERMER, probably the best characterization of the scalp distribution of the MERMER is in terms of the difference in brain activity when an item that is noteworthy to an individual is processed, as compared with the brain activity when an insignificant item is processed. With respect to difference waveforms (target minus irrelevant and, for a guilty subject, probe minus irrelevant) the distribution is typically as follows. During the early positive facet of the MERMER, the response is largest at the central area, followed by the frontal and parietal areas in that order. During the late negative facet of the MERMER, the response is largest at the frontal area, followed by the central and parietal areas in that order.

On the other hand, when differences among trial types are not taken into account, the raw voltage potentials (compared to a pre-stimulus baseline) of both the earlier positive aspect and the late negative aspect of a MERMER elicited by a probe or target stimulus are widespread. The former is generally largest at the parietal area, followed by the central and frontal areas in that order. The latter is generally slightly larger at the parietal area than at the frontal area, and smallest, again by a narrow margin, at the central area. Scalp distributions do vary, and the pattern is further complicated by the fact that the offset of the parietal positive aspect and, at MERMER tend to be earlier at the frontal site than parietally or centrally.

A method of computing and displaying the waveforms that tends to clarify the distinction between innocent and guilty subjects, and typically has the same scalp distribution for a guilty subject as the above-described difference waveforms, is one that produces the "normalized" waveform, consisting of the probe waveform minus the average of the target and irrelevant waveforms. This method produces a waveform that has the characteristic shape and distribution of a MERMER for a guilty subject, and a waveform with an approximately opposite shape and distribution for an innocent subject. Such a method illustrates, in effect, the degree to which the probes resemble either the targets (indicating a guilty determination) or the irrelevants (indicating an innocent determination). The correlation and covariance of normalized waveforms, at all scalp locations combined, with a known template are powerful indicators of the presence or absence in the brain of specific information relevant to the probe stimuli.

FIG. 1 is a plot of normalized waveforms for a "guilty" response containing a MERMER. The normalized average brain responses plotted here were recorded in response to FBI-relevant phrases and acronyms flashed on a computer screen, recorded from three locations on the head: frontal (Fz, solid line), central (Cz, dotted line), and parietal (Pz, bold line). The subject gave no overt indication of recognizing the phrases, but the brain clearly signaled that they were recognized and noteworthy. The large brain MERMER, recognizeable here by a large positive voltage potential followed by a large negative voltage potential at all three scalp locations, indicates that the FBI-relevant stimuli are relevant for this subject. A subject unfamiliar with FBI training would not recognize these stimuli as significant or different from irrelevant stimuli, and would not display a MERMER in response to them. Thus, it can be determined that this subject is an FBI agent (defined in this experiment as a "Guilty" determination).

Figure 2:
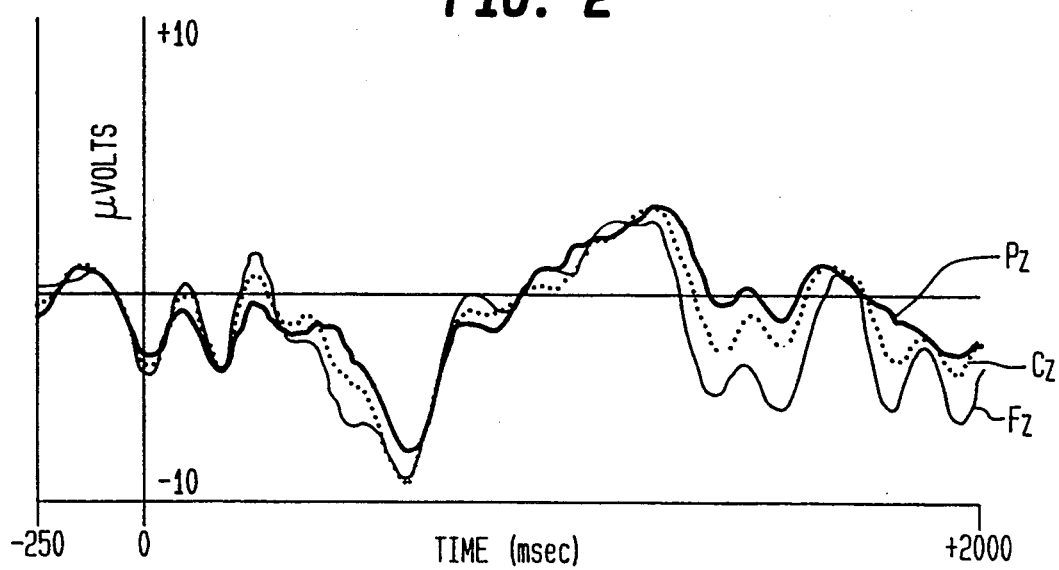
FIG. 2 is a plot of normalized responses to FBI-relevant stimuli, from a subject NOT knowledgeable about the FBI, containing a pattern approximately opposite to that of FIG. 1 revealing LACK of the relevant knowledge (an "innocent" determination).

FIG. 2 is a plot of normalized waveforms for an "Innocent" response. The normalized average brain responses shown here were recorded in response to the same FBI-relevant words as were presented to the subject whose responses comprise FIG. 1, and from the same scalp locations. The normalized responses show a pattern approximately opposite to a MERMER, demonstrating that this subject did not recognize the FBI-relevant words, and therefore is not an FBI agent (defined in this experiment as an "innocent" determination). (The scale in both FIGS. 1 and 2 is −10 to +10 microvolts ×2250 msec: 250 pre-stimulus to 2000 post-stimulus.)

By including in the data analysis, signal processing, and signal detection methods the newly discovered negative aspect of the MERMER, the newly discovered frontal aspect of the MERMER, the newly discovered morphology and complex scalp distribution of the MERMER, and the newly discovered changes in the frequency domain that characterize the MERMER, discriminations between brain responses can be made far more accurately than was previously possible. Thus, information can be detected and communicated more accurately and reliably.

Previous research, including that reported in the above cited United States patent application incorporated here by reference, focused on detecting the P3 component. All of the detection methods described therein are applicable in detecting the MERMER. Three additional types of signal processing procedures can be applied in the detection of the MERMER: (1) methods that focus on the late, frontally prominent, negative component; (2) methods that focus on changes in the frequency domain; (3) methods that focus on other, sophisticated signal processing techniques (for example, dynamical systems analysis—see Rapp, P. E., Albano, A. M., Schmah, T. I., and Farwell, L. A., Filtered noise can mimic low dimensional chaotic attractors, in press, *Physical Review*); and (4) methods that combine measures derived from (1), (2), (3), and/or the methods described in the above cited United States patent application incorporated here by reference.

The task in data analysis and signal processing is to compare the probe, target, and irrelevant responses. If the probe responses are similar to the irrelevants (no MERMER), then the subject does not distinguish the crime-relevant items, and is determined to be innocent. If the probe responses are similar to the target responses (large MERMER), then the subject is distinguishing the crime-relevant stimuli as such, which only a guilty (or rather, knowledgeable regarding the crime) person could do. Therefore such a subject is determined to be guilty.

Before the responses are compared, several techniques of signal-to-noise enhancement may be applied.

For example, on-line and off-line detection of artifacts caused by at least one of the following may be applied: excessive positive voltage potential, excessive negative voltage potential, excessive range of voltage potential, excessive rate of change in voltage potential, excessive integrated deviation of voltage potential, excessive variance of voltage potential, excessive high-frequency electroencephalographic activity, with separate rejection criteria for eye and electroencephalographic channels.

Eye movements create electrical potentials that interfere with brain-generated electrical patterns measured at the scalp. These are eliminated in one of two ways. 1) Thresholds are set for the absolute value of the eye channel data and for the range of the eye channel during a trial (e.g., 400 microvolt maximum absolute value, 100 microvolt maximum range). If the eye channel data exceed one or both of the thresholds for a given trial, then the trial is rejected. 2) A regression procedure is applied that estimates the contribution of the eye movements to activity at each of the other channels and subtracts it out (Gratton, G., Coles, M., and Donchin, E. A new method for off-line removal of ocular artifact. Electroencephalography and Clinical Neurophysiology, 1983, 55: 468–484).

Muscle artifacts produce either high frequency activity, or large, slow shifts in electrical potential, or both. To eliminate muscle activity, trials are rejected that have any of the following in any EEG channel: a large voltage shift in any channel (range or absolute value threshold, e.g., 200 microvolt absolute value, 100 microvolt range); a change with too great a slope (e.g., change between 2 consecutive digitized points exceeds a criterion of, for example, 20 microvolts in 5 microseconds); excessive mean absolute deviation (e.g., 25 mircovolts); excessive standard deviation or variance in the data; excessive high frequency activity (as determined by a discrete Fourier transform). (Thresholds may be determined by instructing a subject to make small facial muscle movements, eye movements, and blinks, computing this parameter, and setting the threshold 10% below the value resulting from the computatons).

A baseline of about 250 msec prior to stimulus onset is subtracted from each waveform, to correct for baseline difference caused by DC drift or other factors.

Individual trials may also be displayed off-line, inspected, and rejected if visual inspection reveals artifacts not detected by the computerized artifact-rejection processes.

Data may also be digitally filtered to eliminate high frequency noise. An optimal, equal-ripple, linear phase, finite impulse response (FIR) filter with a passband cutoff frequency of 6 Hz and a stopband cutoff frequency of 8 Hz provides excellent results (Farwell, L. A., Martinerie, J. M., Bashore, T. R., and Rapp, P. E., Optimal digital filters for long latency event-related brain potentials. *Psychophysiology*, 30, 1993: 306–315). Such a filter is applied to the signals in the course of processing in the time domain, but not in the frequency-domain signal processing, since it may eliminate signals in the frequency domain that contribute to the characterization of the MERMER.

During data collection, the stimuli are displayed to the subject on one video monitor 120, and the experimenter views another monitor 130 (or, in some cases, two or three monitors). Operator displays include 1) the same thing the subject sees, 2) summary textual information, and 3) waveform displays.

The operator's monitor 130 presents some or all of the following waveform displays: ongoing EEG for up to 3 channels, plus one channel of eye movement data; continually updated target, probe, and irrelevant average waveforms, overplotted, for any channel; averages of each trial type in a separate frame with up to 4 channels overplotted. On-line averages only include the artifact-free trials, although all trials are recorded.

The operator's monitor 130 also includes the following textual information: counts of total trials and total trials of each trial type (i.e., target, probe, and irrelevant); counts of artifact-free trials and artifact-free trials of each trial type; status of the current trial—artifact-free, or artifact detected, and which artifacts are detected on this trial; continually updated reaction times by trial type; percentage of correct button press responses by trial type; trial type of the current trial; stimulus presented on the current trial.

When one or more blocks of trials, typically about 75 trials per block, have been presented, then the data are analyzed. The first level of analysis is a visual comparison of the waveforms to provide a rough estimation of whether the probe response is more similar to the irrelevant response (innocent) or the target response (guilty). Then an iterative sampling bootstrapping signal processing method across single trials is applied to arrive at a determination of guilty (knowledgeable regarding the situation under investigation) or innocent (not knowledgeable) and a statistical confidence for the determination. Eye movement rejection or correction, artifact rejection, and digital filtering typically precede the other signal processing procedures.

The analysis may also include pairwise correlation of responses to the stimulus types to detect similarity between the probe response and at least one of the target and irrelevant responses.

The basic method is as follows.

A) Iterative sampling

1) T target trials, P probe trials, and I irrelevant trials, with T, P, and I being equal to the total number of trials of the respective types, are sampled with replacement.

2) These trials are averaged by trial type, yielding three average waveforms. The average waveforms are compared according to a method to determine if the probe average is more similar to the targets or to the irrelevants (or if the probes are different from the irrelevant trials in the direction of the targets).

3) The above procedure is repeated multiple times (usually 100 iterations). Each iteration yields a new set of 3 averages containing probe, target, and irrelevant trials respectively. A tally is kept of the number of times the probe average is more like the irrelevant average than like the target average.

4) The tally is compared to a decision criterion to determine whether or not the information signaled by the probe stimuli has been previously stored in the brain of the subject. A typical criterion is, if the probes are more similar to the irrelevants than to the targets in less than 10% of the iterations, the subject is determined to be guilty. If the probes are more similar to the irrelevants in more than 70% of the cases, the subject is determined to be innocent. A statistical confidence level for the determination of whether or not information signaled by the probe stimuli has been previously stored in the brain of the subject may also be determined.

In addition to displaying the results of the analysis on the monitor 130, the system may also print out on a printer 170 the statistical results, the summary textual information, and the waveform displays, all of which are described above.

B) Comparison Methods in Data Analysis

The basic data analysis and signal processing method to compare the responses to the three stimulus types is described in the above cited United States patent application incorporated here by reference. Several new additions are included here. First of all, the previous data analysis methods were for the purpose of detecting a P3, rather than a MERMER. Thus, they ignored 1) data in the later part of the MERMER, in particular the late negative facet of the MERMER; 2) data from the frontal area of the scalp (again, the late negative facet of the MERMER is prominent here); and 3) frequency domain data.

P3s have been measured using base-to-peak, peak-to-peak, area, stepwise discriminant analysis, covariance with a template, and correlation. All of these metrics can be applied to the late negative potential, and to the combination of the parietal positive and frontally prominent late negative aspects of the MERMER simultaneously. (For area and peak computations, of course, the sign needs to be reversed for the negative component, i.e. absolute value area, and peak.) This analysis can be conducted at the frontal, central, and parietal areas separately or in combinations. (Additional scalp locations, e.g., F3, F4, C3, C4, P3, and P4, may also add more information.)

All of these metrics can be computed on averages of all trials of each type, and/or applied in conjunction with iterative sampling procedures such as bootstrapping. They can be applied to the unadjusted waveforms; to centered (or, in the case of correlation, double-centered) waveforms (that is, waveforms with the grand average waveform subtracted); and/or to difference waveforms (e.g., irrelevant waveform subtracted, or average of irrelevant and target waveform subtracted from probe waveform).

In the preferred embodiment, one metric in the time domain—namely bootstrapping comparison of double-centered probe-target and probe-irrelevant correlations for the epoch from 300 to 2000 msec post-stimulus, at Fz, Cz, and Cz scalp locations—provides for excellent discrimination, which may be further improved by the frequency-domain method described below. The analysis epochs can be adjusted, based on factors including onset and offset of the components of interest.

The results of multiple metrics, both in the time and frequency domains, can be combined in various ways, including conversion to z-scores and averaging, Bayesian statistics, multiple regression, stepwise discriminant analysis, simple averaging (of comparable metrics), voting methods in which a final determination is made based on the majority rule (or a weighted vote) of several determinations made with different metrics, and a choice of the optimum single method for a given data set based on the comparison of the performance of several methods in detecting known patterns.

Another innovation introduced here is frequency-domain analysis of phasic changes in response to specific stimuli, conducted in conjunction with time-domain analysis. The responses to each stimulus (i.e., for 2000 msec or 512 data points at a 256-Hz digitizing rate) are transformed to the frequency domain. The transformation can be to one frequency power spectrum for the entire epoch, or to time frequency data in which a separate frequency power spectrum is computed for each time point, taking into account the entire epoch in each case (see Linear and quadratic time frequency signal representation, *IEEE Signal Processing Magazine*, April, 1992: 21–67). These frequency data are then compared to make the distinctions between the responses to the three stimulus types. Frequency data, like time-domain data, can be averaged, with or without bootstrapping, across single trials. All of the comparison and statistical methods applied to the time-domain data can also be applied to the frequency-domain data. In addition, inferential statistics such as chi-square can be applied to draw conclusions regarding the similarities and differences in the different responses.

In the preferred embodiment, the frequency-domain data are compared using bootstrapped correlations, in the same manner as bootstrapping is applied to the time domain data. Each point, of course, represents the power in a frequency bin, instead of the voltage at a point in time. Additional analysis methods in the frequency domain include 1) computing the pre-stimulus/post-stimulus difference or ratio of power spectra, and substituting this for the post-stimulus power spectrum in data analysis; and 2) computing time-frequency data and analyzing these with the same methods as are applied to the time series.

The frequency-domain characteristics of the MERMER comprise at least one of the following: an increase in power from 0.1 to 4 Hz, a decrease in power from 8 to 12 Hz, and an increase in power from 12 to 20 Hz. It will be appreciated that the pattern may vary for different subjects, that the frequency data and the time frequency data contain additional information beyond the simple pattern described above, and that these variations and additional information can contribute to the discriminations between signals through the use of the correlation processes and other signal-processing techniques described above. Since said signal-processing methods compare responses from the same subject to different stimuli, it is possible for complicated patterns that may be idiosyncratic to nevertheless contribute to the discrimination that these signal-processing techniques provide. It will be understood that the MERMER as a phenomenon may contribute to the distinctions between brain responses in a manner that includes more than the simple characterization stated above.

The Farwell MERA Brain Communicator

From the above discussion it is clear that MERA, and in particular the MERMER, can be used to detect information that is noteworthy to an individual due to his past activities, experience, and/or associations. The MERMER can also be used to communicate information that is noteworthy to an individual as a result of his present desires, intentions, or choices. In this way an individual can communicate with a computer without involvement of the motor systems. The computer can then convey the brain's command to another device, such as a speech synthesizer or a robot, to accomplish a direct brain-to-machine communication and command link.

The procedure is as follows. Options are presented to a subject in the form of visual stimuli that are flashed or intensified briefly on a computer screen (e.g., words, icons, or pictures are flashed for 300 msec at an inter-stimulus interval of 2000 msec). The visual images may be flashed one at a time, or several images may be on the screen at a time. In the latter case, the different images may be intensified individually or in groups, at different times. For example, the groups that are selectively intensified may consist of the rows and columns of a matrix. Another alternative is to present words in the auditory modality.

The subject is instructed to pay particular attention to the item he wishes to communicate, and to think specifically about its meaning and past associations from the time it appears until the occurrence of the next stimulus. The brain information processing undertaken in response to the option chosen results in a MERMER, which is lacking in the responses to the unchosen items.

The brain responses to the various options are compared to see which option elicits the most substantial MERMER. This option then constitutes a command to the computer. The computer can be programmed to respond to this command by producing speech through a speech synthesizer: signaling a robot to perform mechanical tasks; activating or modulating other electronic equipment such as televisions, radios, telephones, etc.; and controlling other mechanical devices such as a powered wheelchair.

The following procedure and equipment are used when the system is used to control a robot and a speech synthesizer.

Referring again to FIG. 6, the hardware used includes a 486 PC with a serial port 110 (Gateway 2000 486/33 Personal Computer), a LabMaster DMA analog I/O card (from Scientific Solutions; with Software Toolkit manual), a HERO 1 robot with arm/gripper assembly 180 (HERO 1 robot from HEATH Company, with ET-18 robot technical manual and ET-18 robot users guide), and a MENOS 1 communications card ( from Virtual Devices Inc., with MENOS 1 Users Manual). Standard RS232 communications protocol was used to download executable files into the robot. A phone wire was used to connect the digital I/O port on the LabMaster board with the digital I/O port on the robot.

Since RS232 communications could only be used during development and not during run-time, robot/PC hardware run-time communications were achieved through a parallel interface using polled I/O. The robot had built in parallel I/O functions while the PC had a LabMaster DMA card for this purpose. The following diagram describes each bit of the interface.

| PC side | Robot side |
|---|---|
| Output: Task select bit 0 → | Input bit 0 |
| Output: Task select bit 1 → | Input bit 1 |
| Output: Task select bit 2 → | Input bit 2 |
| Input: Clear to Send | ← Output: Rdy for Cmd |
| Input: Command rec'd | ← Output: Command buffered |

Commands were transferred using the task bits while handshaking was accomplished using the Clear to Send bit which the PC software waited to see clear before initiating a command transfer. Before changing the bit pattern sent as a command, the PC waits for the Command rec'd line to clear. Otherwise the PC could send a command and deassert the task bit lines before the robot (which runs very slowly) has had a chance to buffer the command.

The speech synthesizer system 190 from DEC includes a board for the PC and a speaker to place on the robot (DECtalk PC text-to-speech system from Digital Equipment Corporation). Connections were made with a standard mini audio cable.

Code is written in 80386 assembler and 'C' for the PC while the robot uses a mix of 6801 assembler and a special purpose robot language developed by HEATH (ET-18 robot technical manual, ET-18 robot users guide, from Heath).

The speech synthesizer may be controlled by a DEC provided DOS driver which is accessed by our program using a DOS command line within 'C' code.

Once the operator has selected an option, the PC software issues commands to the robot and speech synthesizer.

Speech is activated by invoking a DOS command line using the DEC DOS driver.

Command of a robot may be achieved by sending a specific bit pattern to the software running on the robot. Once the robot sees a bit pattern other than the do nothing pattern, it begins to carry out the specified task. During the performance of the task the robot looks for new commands that may be sent by the PC and buffers them for later execution in the command queue. Once the current command is finished the robot will look at the queue for its next command. If the queue is empty the robot will return to a wait state looking for a new command.

Each robot command may cause the robot to move in a certain sequence of motions followed by a return to an initial starting position.

The PC may be used as a host development system for the robot. Once HEX files are created using Enertec, HEX files may be downloaded to the robot using the windows based "terminal" program. A ROM based terminal control program called "l'il bug" on the MENOS board in the robot provides downloading capability. A special purpose robot control language provided by HEATH may resides in ROM within the robot. 6801 assembler source code may be mixed with robot control language commands by declaring them as HEX data blocks. This way the entire routine can be assembled without the assembler trying to interpret the special robot commands. Debugging may be done using the Borland Turbo Debugger on the PC while on the robot all debugging was done via the HEX keypad on top of the robot.

It will be appreciated that other processes and devices could also be used.

The Farwell Velcro-Positioned Electrode Headband

The Velcro-positioned electrode headband 150 (see FIGS. 3 and 4) retains the fabric structure of the basic headband, described in the above cited United States patent application incorporated here by reference. (Velcro, according to Webster's New World Dictionary, is a trademark for a nylon material made with both a surface of tiny hooks and a complementary surface of an adhesive pile typically used in garments in matching strips that can be pressed together or pulled apart for easy fastening and unfastening.) That is, the dimensions and fabric assembly of the basic headband are employed. It is believed that the headband design described here is preferred, but it will be appreciated that other means for collecting brain signals, including those described in applicant's above cited U.S. patent application are also suitable. The snaps that hold the electrodes themselves, however, are not fixed into the holes in the fabric's surface. Instead, they can be positioned individually by attaching the Velcro hook pad sewn onto each to an additional thin pad of Velcro loops sewn into the posterior side of the headband. The optimal approximate dimensions of the hook pad sewn to the electrode are 1" long (measuring along the electrode wire below the electrode) and 0.5" wide (measuring perpendicularly to the wire).

Figure 3:
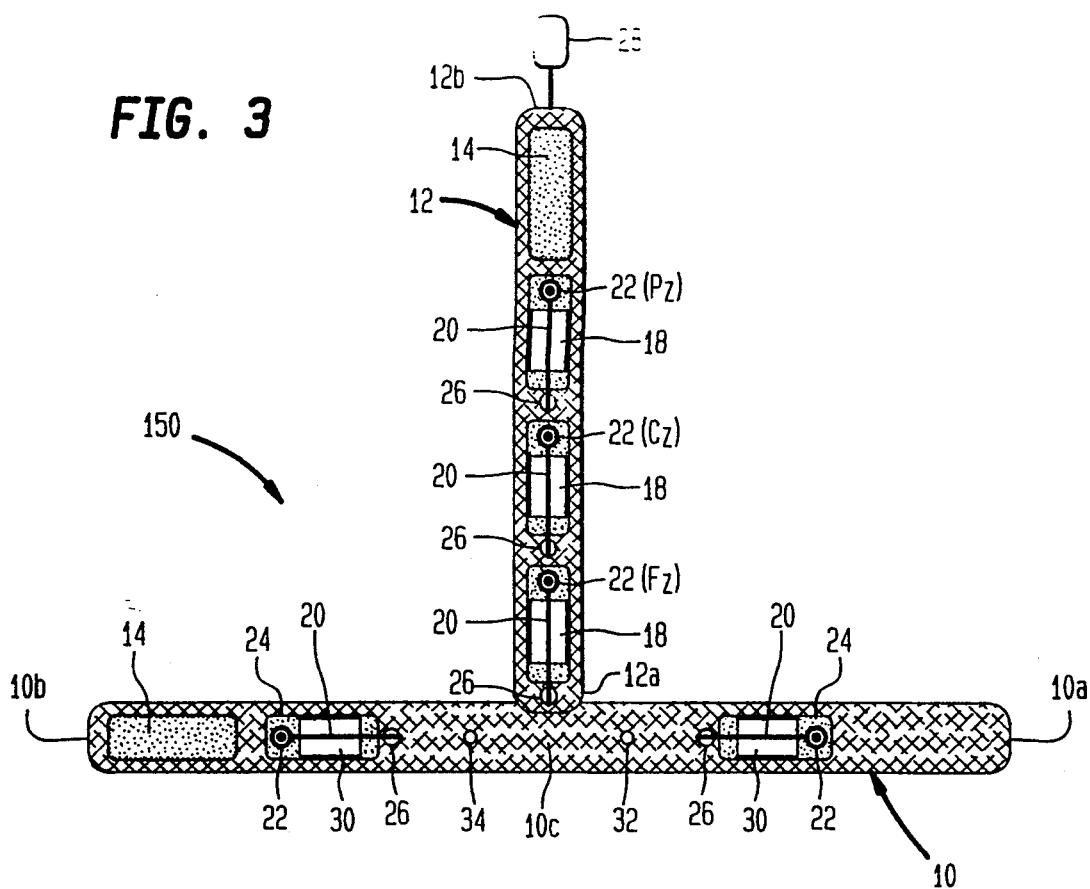
FIG. 3 is a schematic of the posterior side of the Velcro-positioned electrode headband, showing the concept and placement of the Velcro-positioned electrodes, their hook flaps and the attached long, thin loop pads, as well as the basic Velcro hook pads for overall headband fastening.
Figure 4:
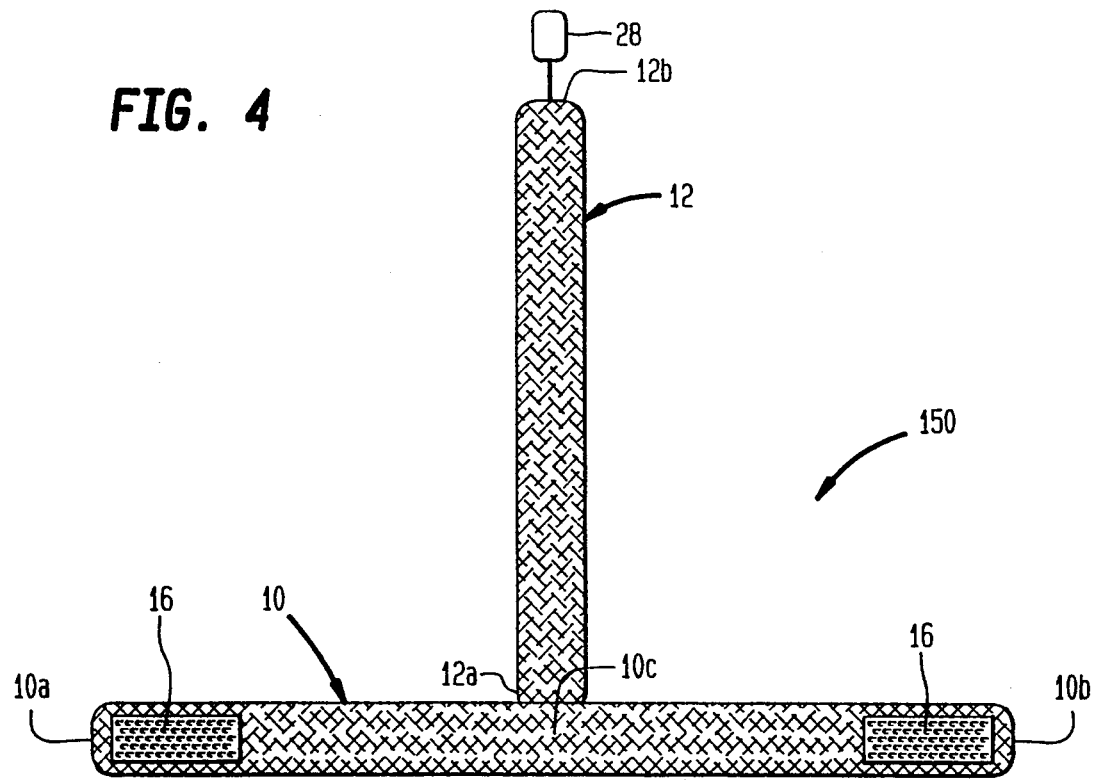
FIG. 4 is a schematic of the anterior side of the Velcro-positioned electrode headband, showing Velcro positioning and fabric structure identical to that of the Basic Headband.
Figure 5:
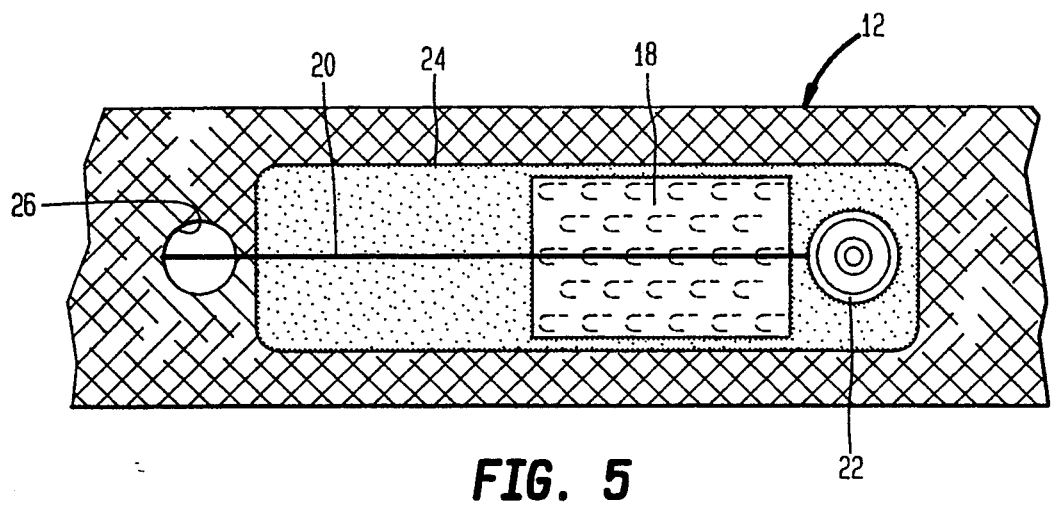
FIG. 5 is a schematic of the structure of one individual Velcro-positioned electrode, indicating Velcro positioning, location of fabric hole, path of electrode wire, and position of electrode.

More specifically, the headband 150 is illustrated in FIG. 6 positioned over the scalp of a subject, with the details of the headband 150 being illustrated in more particularity in FIGS. 3-5. FIG. 3 illustrates the posterior side of the Velcro-positioned electrode headband 150, and FIG. 4 illustrates the anterior side thereof. A brief summary of significant features of the headband 150 include:

1) Assured sizing through extreme structural flexibility;
2) Assured placement of electrodes by affixing them to a highly flexible super-structure;
3) Construction of a comfortable cloth material that stretches easily;
4) Disposable electrodes affixed to the headband by snaps;
5) Electrodes wires running within the headband sheath;
6) A strap that wraps around the head from the forehead to the back of the head and a second strap that crosses from the front to the back of the head, to position electrodes across the midline of the scalp;
7) Fastening of the two ends of the band the third end of the "overflap" strap with Velcro at the back of the head;
8) Wires to conduct the brain signals, running inside of the cloth straps to a connector that can be connected to a cable leading to an EEG amplifier;
9) Snaps at the desired electrode locations on the headband, inclusive of at least one of the following: Fz, Cz, Pz forehead ground; forehead eye movement lead; left mastoid, and right mastoid; and 10) Velcro pads affixed to the headband and the snaps, so that the position of the snaps, and the electrodes that attach thereto, can be adjusted.

Referring to FIGS. 3 and 4, the headband 150 includes a flexible band 10 also referred to as a crossbar or strap which has first and second opposite ends 10a, 10b and a center portion 10c therebetween. The band 10 is sized to have a suitable length to surround the subject's scalp as shown in FIG. 6 for joining together the first and second ends 10a,b with the right side of the band 10 (which includes the band first end 10a) configured for placement over the right mastoid, and the left side of the band 10 (which includes the band second end 10b) configured for placement over the left mastoid. A flexible overflap 12 also referred to as a strap is integrally joined to the band 10 in a general T-configuration. The overflap 12 includes first and second opposite ends 12a, 12b, with the overlap first end 12a being integrally joined to the band center portion 10c. The overflap 12 is sized for having a length to extend over the scalp frontal, central, and parietal locations as shown in FIG. 6 for joining together the overflap second end 12b to the joined-together band first and second ends 10a, 10b.

More specifically, first and second means are provided for releasably joining together the band first and second ends 10a, 10b and the overflap second end 12b with the joined-together band first and second ends 10a,b. In the preferred embodiment illustrated in FIGS. 3 and 4, cooperating Velcro pads or strips are used. As shown in FIG. 3, the posterior side of the headband 150 includes similar Velcro loop pads 14 illustrated as rectangles with curved corners suitably attached to the respective second ends 10b and 12b of the band 10 and overflap 12, respectively. FIG. 4 illustrates complementary Velcro hook pads 16 suitably attached to the anterior side of the headband 150 at the band first and second ends 10a, 10b. The hook pads 16 are illustrated as rectangles with sharp corners to distinguish them from the loop pads 14. The Velcro loop and hook pads 14, 16 allow the band 10 to be configured around the scalp of the subject (see FIG. 6) and held in place by the cooperation thereof. The overflap 12 extends over the midline of the scalp, with the loop pad 14 on the second end 12b thereof being joined to the hook pad 16 on the second end 10b of the band 10. In this way, the headband 150 is positioned over the scalp of the subject, with the overflap 12 extending along the scalp midline.

In order to adjust the position of electrodes carried by the headband 150, the headband 150 includes a plurality of support or first pads 18 each having an electrode wire 20 fixedly joined or sewn thereto, with a conventional electrode snap 22 joined to the distal end of the wire 20 for mounting an electrode (not shown) thereto. Three pads 18 are illustrated, with three snaps 22 for receiving disposable electrodes (not shown), which are positionable at the frontal (Fz), central (Cz), and parietal (Pz) scalp locations. The snap 22 allows replacement of electrodes as is conventionally known. Additional means in the form of Velcro pads are used for releasably joining the first pads 18 to the posterior side of the overflap 12 as shown in FIG. 3 for allowing position adjustment of the electrode snaps 22 along the overflap 12, and thereby obtain position adjustment of the electrode snaps 22 and the electrodes joined thereto, relative to the midline of the scalp.

FIG. 5 illustrates an exemplary one of the three support pads 18 joined to the overflap 12 illustrated in FIG. 3. The first pads 18 themselves are preferably in the form of Velcro hook pads shown as sharp cornered rectangles similar to the hook pads 16 illustrated in FIG. 4. The joining means further includes a complementary Velcro loop pad 24 fixedly joined or sewn to the overflap 12 and is illustrated in the exemplary form of an elongated rectangle having rounded corners similar to the Velcro loop pads 14 illustrated in FIG. 3. In this way, the position of the first pads 18 may be adjusted as required along the length of the loop pads 24 for adjusting the position of the electrode snaps 22 thereon and in turn the electrodes joined thereto. The first pads 18 may be readily pulled away from the loop pads 24 and rejoined thereto to effect position adjustment.

The overflap 12 illustrated in FIGS. 3–5 includes holes 26 on the posterior side thereof through which the respective electrode wires 20 run. The overflap 12 is in the exemplary form of a sheath having a passage therein through which the electrode wires 20 may run from the holes 26 to a mouth at the overflap second end 12b. The electrode wires 20 have proximate ends suitably joined to a conventional DB9 female connector 28 disposed adjacent to the overflap second end 12b, which connector 28 is in turn electrically joined to the EEG amplifier system 140 (see FIG. 6).

The several loop pads 14 and 24 are preferably elongate and longer than the cooperating hook pads 16 and 18 for allowing position adjustment of the hook pads 16, 18 along the respective loop pads 14, 24. In this way, the headband 150 may be adjusted for different scalp sizes, with corresponding adjustment of the electrode snaps 22 to the frontal (Fz), central (Cz), and parietal (Pz) scalp locations.

Referring again to FIG. 3, the headband 150 preferably also includes a plurality of second support pads 30 each also having an electrode wire 20 fixedly joined or sewn thereto, with a corresponding electrode snap 22 joined to the distal end thereof for mounting a cooperating electrode (not shown) thereto. Two of the second pads 30 are illustrated in FIG. 3 and are releasably joined to the band 10 for allowing position adjustment of the second pad electrode snaps 22 along the band 10. Preferably, the second pads 30 are releasably mounted identically to the first pads 18 on the overflap 12, and therefore additional ones of the Velcro loop pads 24 are sewn to the band 10, with the second pads 30 being in the form of cooperating hook pads. The two second pads 30 illustrated in FIG. 3 are suitably positioned for locating respective electrodes adjacent to the left and right mastoid locations of the subject's scalp.

Two additional electrode locations are provided on the band 10 as illustrated in FIG. 3 and include a conventional ground electrode 32 and a conventional electro-oculogram (EOG) electrode, which are conventionally fixed to the posterior side of the band 10 adjacent to the respective right and left mastoid scalp locations, respectively.

In order to adjust the Farwell MERA System to meet the requirements of specific applications, numerous modifications may be made in the basic design specified above.

Digitizing rate, stimulus duration, inter-stimulus interval, and other timing parameters may be varied.

Electro-oculographic (EOG) activity may be collected not only by electrodes above and below one eye, but also by lateral EOG electrodes. Alternatively, one electrode above the eye, (referred to the mastoids, to a non-cephalic reference, or to another reference on the head) may be used to replace the electrodes above and below the eye.

Instead of visually presented words, pictures that are digitized and displayed on a video monitor may be used. Also, moving video pictures may be used, with particular critical events time stamped and the EEG activity time-locked to those events analyzed. Stimuli may also be presented through the auditory modality, e.g., through use of digitized speech or other sounds presented through a digital to analog converter, amplifier/attenuator, and speaker system. Auditory stimuli may be entire sentences instead of short phrases. Here again, certain critical words or auditory events are time stamped so that the corresponding EEG activity can be analyzed. In the case of moving video pictures or digitized auditory activity, a stimulus may last for a number of seconds or longer, rather than for only a fraction of a second.

The embodiment described above referred to the use of this system to investigate whether or not an individual had information stored in the brain regarding a particular event, e.g., a crime, when the investigator knows what the information is and can therefore construct appropriate stimulus sets. The same system can be used for a different kind of information detection, when the investigator does not know certain information, but knows or suspects that the subject possesses the information. If the information in question can be reduced to a multiple choice presentation, then the correct information can be detected on the basis of the MERMER.

Say, for example, that an investigator suspected that a captured spy knew of a plot to assassinate a particular American political leader, but the investigator did not know where, when, or the identity of the intended victim; or, it was suspected that an individual knew of a plot to blow up a particular airliner at a particular time, but investigators had been unable to determine which specific plane would be hit.

A stimulus set could be constructed consisting of 1) rare, target stimuli to which the subject was instructed to respond in some way (e.g., push a particular button), and 2) frequent, non-target stimuli. The non-target stimuli could contain a number of different possible relevant stimuli (in effect, "probes"), but the examiner would not know which stimuli were relevant. If the subject did have particular knowledge regarding certain stimuli—e.g., if the name of the intended assassination victim, known to the subject but not to the examiner, were presented—this would constitute a noteworthy event, and could be expected to elicit a MERMER. The other non-target stimuli, having no major significance in this context, would be expected not to elicit a MERMER (like the irrelevants in the original embodiment).

Instead of comparing a known probe with targets and irrelevants, data analysis in this case would compare each of the non-targets—all possible "probes"—with the other non-targets (presumably mostly irrelevant) and with the targets (known to be rare and relevant as a result of experimental instructions). The relevant item, if any, would be detected as the non-target item that elicited a large MERMER, similar to the target response and in contrast to the response to the other non-targets.

In such a case, one could detect information that was not known to the examiner in advance, provided that the examiner knew enough about the kind of information that might be relevant to construct an appropriate multiple-choice test. Given that many modern college students graduate from college on the basis of an accumulated data base virtually all of which has been reduced to a multiple-choice format for presentation on computer-scored tests, such a technology shows some promise of being capable of detecting large amounts of concealed information.

One of the innovations introduced in the above cited United States patent application incorporated here by reference is the use of target stimuli that are a subset of the items that are relevant to the information detected (that is, are a subset of the items that could have been used as probes), instead of a subset of the irrelevant items. This is particularly useful when the stimuli are acronyms. Known acronyms are more quickly recognized than nonsense strings of letters. As a result, the latency of the brain response to an acronym that is recognized as such by the subject is less than that of the brain response to a nonsense letter string. Since irrelevants, for all subjects, are nonsense letter strings, the brain responses to irrelevants will tend to be of a relatively long latency. If the targets and probes are both acronyms that will be recognized only by an individual who has the specified knowledge being tested, then in such an individual both targets and probes will tend to elicit a shorter latency response than irrelevants. Probes, then, will be more similar to targets than to irrelevants in response latency, and thus latency as well as amplitude of the response will contribute to the determination in the case of a guilty subject. (For an innocent subject, all three stimulus types will be nonsense strings—the targets having been recently learned only for the purpose of the test—and there will be little difference in response latency.)

If, on the other hand, an experimental design is used wherein targets and irrelevants are both nonsense syllables, and probes are acronyms that would be recognized only by a guilty subject, then a guilty subject will have a shorter-latency response only to the probes and not to the targets or the irrelevants. Thus, the latency distinctions will tend to make the probe and target responses different from each other, and the discrimination will not be as clear as the above-described case when the probes and targets have shorter latency in common for a guilty subject. (Here again, for an innocent subject all three trial types will be nonsense syllables, and the phenomenon of a shorter latency response to acronyms will not come into play.)

Since eye movements, and blinks in particular, produce scalp potentials that interfere with measurements of brain electrical responses, and since subjects cannot go indefinitely without blinking, it is useful to inform the subject of a certain period of time when blinks will cause the least interference. With an inter-stimulus-interval of 2900 msec and a prestimulus baseline of 250 msec, the subject can blink between 1800 and 2700 msec post-stimulus with a minimum of interference with the signals of interest. During this interval, on-line artifact rejection can be disabled. (Data can be collected during this interval, for use in off-line analysis which included eye-movement correction.)

The subject may be informed of this approximate time range. Alternatively, a fixation point may appear during this interval at the center of the area where the stimulus will next appear, and the subject may be informed that when the fixation point is on the screen it is all right to blink (and otherwise, just to direct his gaze to the point). This has the added benefit of fixing the subject's gaze immediately prior to stimulus onset, thus minimizing eye movement artifacts that could occur when a subject whose gaze had not been centered moved his eyes to acquire the stimulus.

In the event that a fixation point is so used, it is important that it continue until stimulus onset or very close to stimulus onset, so that potentially contaminating brain responses are not generated at the offset of the fixation point. With timing parameters as specified above, any responses generated by fixation pint onset will take place during the interval after the response to one stimulus and before the baseline of the next trial. (In any case such responses, if any, will not contribute differentially to the different trial types.)

One method of taking into account differences in brain response latency is to define the data analysis epoch as the period of time when the target response is different from the irrelevant response, i.e., from the beginning of the longest continuous epoch when the target response voltage is more positive than the irrelevant response voltage (beginning of P3) to the end of the longest time period when the target response voltage is more negative than the irrelevant response voltage (end of the late negative potential). This can be defined at any one channel, or at the channel or channels where each of the facets of the response is largest.

Experimental

The Farwell MERA System was applied in the detection of FBI new agent trainees using FBI-relevant probes. The system correctly classified 100% of the 17 FBI new agents tested, as well as 4 control subjects who were "innocent" of any knowledge regarding the FBI.

The results of the study of FBI agents were as predicted in every respect. In every case, FBI agents showed large MERMERs in response both to the targets and to the FBI-relevant probes. The subjects who were not knowledgeable regarding the FBI showed large MERMERs only to the targets.

Bootstrapping analysis was conducted to make a determination of whether the subject was knowledgeable regarding the FBI (a "guilty" determination), or was "innocent" of such knowledge. The Farwell MERA System yielded a correct determination in every case, both for the FBI agents and for the control group, along with a statistical confidence for the determination. The determinations are summarized in Table 1. The determinations and the statistical confidence for each are listed in Table 2.

As can be seen in Tables 1 and 2, 100% of the determinations were correct. There were no false positives, no false negatives, and no indeterminates.

TABLE 1
FARWELL MERA SYSTEM:
SUMMARY OF DETERMINATIONS

| Determination | Subject State | | |
|---|---|---|---|
| | Innocent | Guilty | Total |
| Innocent | 4 | 0 | 4 |
| Guilty | 0 | 17 | 17 |
| Indeterminate | 0 | 0 | 0 |
| Total | 4 | 17 | 21 |

| Predictive Values | |
|---|---|
| Positive | Negative |
| 100% | 100% |

| Validity (excluding inconclusives) | 100% |
|---|---|
| Validity (including inconclusives) | 100% |

TABLE 2
FARWELL MERA SYSTEM:
DETERMINATIONS AND
STATISTICAL CONFIDENCE

| Subject Number | Determination | Statistical Confidence |
|---|---|---|
| A. FBI Agents ("Guilty") | | |
| 1 | Guilty | 100 |
| 2 | Guilty | 100 |
| 3 | Guilty | 100 |
| 4 | Guilty | 100 |
| 5 | Guilty | 100 |
| 6 | Guilty | 92 |
| 7 | Guilty | 100 |
| 8 | Guilty | 92 |
| 9 | Guilty | 100 |
| 10 | Guilty | 98 |
| 11 | Guilty | 98 |
| 12 | Guilty | 100 |
| 13 | Guilty | 97 |
| 14 | Guilty | 91 |
| 15 | Guilty | 100 |
| 16 | Guilty | 100 |
| 17 | Guilty | 100 |
| B. Non-FBI Agents ("Innocent") | | |
| 1 | Innocent | 90 |
| 2 | Innocent | 100 |
| 3 | Innocent | 100 |
| 4 | Innocent | 74 |

Applicant's invention has been described above in terms of specific embodiments. It will be readily appreciated by one of ordinary skill in the art, however, that the invention is not limited to those embodiments, and that, in fact, the principles of the invention may be embodied and practiced in devices and methods other than those specifically described above. Therefore, the invention should not be regarded as delimited by these specific embodiments, but by the following claims.

I claim:

1. A method of detecting concealed information stored in the human brain through multifaceted electroencephalographic response anaysis (MERA) comprising the steps of:
   1) Presenting stimuli to a subject;
   2) Recording electrical brain responses to the stimuli;
   3) Analyzing said electrical brain responses for uncovering as a first facet an electrically positive P3 component thereof, and as a second facet at least one of a phasic shift in frequency power spectrum thereof, and an electrically negative component thereof following in time said P3 component.

2. The method in claim 1 wherein data signals corresponding to said electrical brain responses to different stimulus types are compared, and the stimuli include:
   1) Irrelevant stimuli ("irrelevants");
   2) Stimuli relevant to the information to be detected, that are not identified in instructions to the subject as being different from the irrelevants, and would not be clearly distinguishable from the irrelevants for a subject lacking the specified concealed information being sought ("probes");
   3) At least one of the following ("targets"):
      a) Stimuli that are identified to the subject as being noteworthy, and in response to which the subject is instructed to perform a task, that are relevant to the information being detected; and
      b) Stimuli that are identified to the subject as being noteworthy, and in response to which the subject is instructed to perform a task, that are NOT relevant to the information being detected.

3. The method in claim 2 wherein the data signals that are collected and analyzed include data signals from brain electrical activity from the time period of 0 to 1400 msec post-stimulus and data signals from brain electrical activity from the time period of 1400 to 2000 msec post-stimulus.

4. The method in claim 3 wherein the data signals include signals corresponding to a widespread late negative component with a substantial frontal amplitude ("late negative component"), and wherein said frontal data signals contribute materially to the analysis.

5. The method in claim 3 wherein the analysis includes bootstrapping across single trails.

6. The method in claim 2 wherein the data signals are collected from more than one scalp location, and a computer-implemented signal processing and analysis method is applied that includes analysis of more than one scalp location.

7. The method in claim 6 wherein the data signals that are collected and analyzed include some data signals from the time period of 0 to 1400 msec post-stimulus and some data signals from the time period of 1400 to 2000 msec post-stimulus.

8. The method in claim 7 wherein the analysis method includes determining
a subsequent negative component with a widespread scalp distribution including a substantial frontal amplitude.

9. The method in claim 8 wherein the analysis includes computation of the correlations between the probe and irrelevant responses and between the probe and target responses.

10. The method in claim 9 wherein the analysis includes bootstrapping across single trails.

11. The method in claim 8 wherein the analysis includes bootstrapping across single trails.

12. The method in claim 7 wherein the analysis includes bootstrapping across single trails.

13. The method in claim 9 wherein the analysis method includes determining:
 1) Base-to-peak amplitude of the P3 and late negative components, at the respective scalp locations where each is maximal;
 2) Peak-to-peak amplitude of the P3 and late negative components, at the respective scalp locations where each is maximal;
 3) Absolute value area of the P3 and late negative components, at the respective scalp locations where each is maximal;
 4) Analysis epochs that can be adjusted, based on factors including onset and offset of the components of interest; and
 5) Pairwise correlation of responses to the stimulus types to detect similarity between the probe response and at least one of the target and irrelevant responses; and the analysis method further includes:
 6) Bootstrapping across single trials;
 7) Combining the results obtained with at least two different comparison metrics;
 8) Determining whether or not the information signaled by the probe stimuli has been previously stored in the brain of the subject;
 9) Obtaining a statistical confidence level for said determination of step (8); and
 10) Collecting data from multiple electroencephalographic channels and at least one channel to record eye movement artifacts.

14. The method in claim 13 wherein frequency domain results are included in the analysis.

15. The method in claim 6 wherein the analysis includes bootstrapping across single trials.

16. The method in claim 2 wherein the analysis includes at least one of the following:
 1) Transformation of the data signals to the frequency domain and comparison of the probe frequency spectrum with at least one of the target and irrelevant frequency spectra;
 2) Computation of time frequency data for at least one of the probe, target, and irrelevant responses.

17. The method in claim 16 wherein the differences between pre-stimulus and post-stimulus frequency spectra are computed and compared for the responses to the probe, target, and irrelevant stimuli.

18. The method in claim 16 wherein time frequency data are computed and compared for the responses to the probe, target, and irrelevant stimuli.

19. The method in claim 16 wherein the frequency domain responses to the probe, target, and irrelevant stimuli are compared using bootstrapping.

20. The method in claim 2 wherein precisely timed visual and auditory stimuli are presented simultaneously.

21. A method of applying multifaceted electroencephalographic response analysis (MERA) comprising:
 1) Making conscious choices by a subject from among at least two options;
 2) Measuring electrical brain activity of said subject in the form of electrical signals that is associated with the choice of options;
 3) Analyzing the electrical signals obtained for uncovering as a first facet an electrically positive P3 component thereof, and as a second facet at least one of a phasic shift in frequency power spectrum thereof, and an electrically negative component thereof following in time said P3 component to detect which option is chosen by said subject; and
 4) Utilizing the information obtained regarding the options chosen to perform a function using a device actuated in response to said chosen option.

22. The method in claim 21 wherein said device is a computer.

23. The method in claim 22 wherein said computer controls a mechanical device having motion capability.

24. The method in claim 23 wherein electrical signals are analyzed from more than one active scalp location.

25. The method in claim 23 wherein the signal analysis includes both analysis in the time domain and analysis in the frequency domain.

26. The method in claim 23 wherein the signals measured are event-related brain potentials including a P3 component.

27. The method in claim 23 wherein the analysis includes at least one of the following: correlation and covariance with a template.

28. The method in claim 23 wherein said device is a robot having motion capability.

29. The method in claim 23 wherein the options chosen among are presented in at least one of the following two modes:
 1) visually presented on a video screen under computer control, and
 2) presented through the auditory modality.

30. The method in claim 22 wherein the options chosen among are presented to the subject by said computer.

31. The method in claim 23 wherein the options chosen among are presented in at least one of the following two modes:
  1) visually presented on a video screen under computer control, and
  2) presented through the auditory modality.

32. The method in claim 22 wherein said computer controls a speaker for communication of verbal material.

33. The method in claim 22 wherein the signal analysis includes both analysis in the time domain and analysis in the frequency domain.

34. The method in claim 22 wherein the electrical signals are measured over a time epoch and the analysis includes at least some of the time epoch between the onset of a stimulus and 600 msec post-stimulus, and at least some of the time epoch between 600 msec post-stimulus and 2000 msec post-stimulus.

35. The method in claim 34 wherein the time epoch analyzed includes at least some of the period between 1000 msec post-stimulus and 2000 msec post-stimulus.

36. The method in claim 22 wherein both positive and negative deflections in the voltage potential of the measured electrical signals contribute materially to the signal analysis.

37. The method in claim 22 wherein electrical signals are analyzed from more than one active scalp location.

38. A method of analyzing electrical brain activity consisting of:
  1) Presenting stimuli to a subject;
  2) Detecting electrophysiological manifestations of information-processing brain activity in response to said stimuli;
  3) Amplifying, digitizing, and analyzing said manifestations of information-processing brain activity;
  4) Applying a computer-implemented signal analysis method that includes analysis in both the time and frequency domains, and mathematically combines the results of said analysis in said two domains to make inferences regarding said information-processing brain activity.

39. The method in claim 38 wherein the brain response analyzed contains a memory and encoding related multifaceted electroencephalographic response (MERMER).

40. The method in claim 39 wherein the MERMER is used for at least one of the following:
  1) Detection of concealed information;
  2) Communication between a brain and a computer;
  3) Communication of verbal material from a brain to a computer, and from the computer to another person through a device that generates verbal output through at least one of the visual and auditory modalities;
  4) Communication from a brain to a computer of commands for the control of a mechanical device; and
  5) Communication from a brain to a computer of commands for the control of a robot.

41. A headband for measurement of electrical brain activity from a scalp of a subject, said scalp having frontal, central, parietal, left mastoid, and right mastoid locations, said headband comprising:
  a flexible band having first and second opposite ends and a center portion therebetween, and being sized to surround said scalp for joining together said first and second ends;
  a flexible overflap having first and second opposite ends, with said overflap first end being integrally joined to said band center portion, and being sized to extend over said scalp frontal, central, and parietal locations for joining together said overflap second end to said band first and second ends;
  first means for releasably joining together said band first and second ends;
  second means for releasably joining together said overflap second end with said joined together band first and second ends;
  a plurality of first pads each having an electrode wire fixedly joined thereto, with an electrode snap joined to a distal end of said wire for mounting an electrode thereto; and
  third means for releasably joining said first pads to said overflap for allowing position adjustment of said electrode snaps along said overflap, and thereby position adjustment of said electrode snaps relative to said scalp.

42. A headband according to claim 41 wherein said electrode wires extend from said first pads and through said overflap, and have proximate ends joined to a connector disposed adjacent to said overflap second end.

43. A headband according to claim 41 wherein said third joining means includes a primary Velcro pad fixedly joined to said overflap, and said first pads are in the form of cooperating secondary Velcro pads for allowing each of said first pads to be releasably joined to said primary Velcro pad.

44. A headband according to claim 43 wherein said primary pad is elongate and longer than said secondary pad for allowing position adjustment of said secondary pad along said primary pad.

45. A headband according to claim 44 further comprising:
  a plurality of second pads each having an electrode wire fixedly joined thereto, with an electrode snap joined to a distal end thereof for mounting an electrode thereto; and
  fourth means for releasably joining said second pads to said band for allowing position adjustment of said second pad electrode snaps along said band.

46. A method of detecting information stored in a brain of a subject comprising:
  presenting to said subject relevant and irrelevant stimuli;
  detecting an electrical brain response from said subject in response to each of said stimuli;
  analyzing said electrical brain responses for uncovering as a first facet an electrically positive P3 component thereof, and as a second facet at least one of a phasic shift in frequency power spectrum thereof and an electrically negative component thereof following in time said P3 component; and
  comparing said electrical brain responses due to said relevant and irrelevant stimuli for detecting said information in said subject brain based on said second facet.

47. A method according to claim 46 wherein said detecting step for each of said stimuli has a predetermined time period selected for initially detecting said first facet and then detecting said second facet.

48. A method according to claim 47 wherein:
  said subject has a scalp with frontal, central, and parietal locations;

said detecting step is effective for detecting said electrical brain responses at said frontal, central, and parietal scalp locations; and said electrical brain responses are characterized by being largest at different ones of said scalp locations for said first and second facets.

49. A method according to claim 47 wherein said second facet includes a frequency power spectrum characterized by power first increasing, decreasing, and then increasing as frequency increases.

50. A method according to claim 47 wherein said detecting step is effective for detecting said electrical brain responses at frequencies below 6 Hz.

51. A method according to claim 50 wherein said detecting step is effective for detecting said electrical brain responses at frequencies between about 0.1 and 2.0 Hz.

52. A method according to claim 47 wherein said stimuli further comprise:
   a Probe stimulus representing relevant specific information to be detected in said subject brain, and effecting said second facet in a subject having knowledge thereof, and not effecting said second facet in a subject not having knowledge thereof;
   a Target stimulus representing information for which said subject is required to perform a predetermined response and which effects said second facet in said subject; and
   an Irrelevant stimulus not relevant to said specific information to be detected in said subject brain and not effecting said second facet in said subject.

53. A method according to claim 52 wherein said comparing step further comprises obtaining a difference in said electrical brain responses for said Probe and Irrelevant stimuli, and obtaining a difference in said electrical brain responses for said Target and Irrelevant stimuli.

54. A method according to claim 52 wherein said comparing step further comprises obtaining a normalized waveform by subtracting an average waveform of said electrical brain responses for said Target and Irrelevant stimuli from a waveform for said electrical brain responses of said Probe stimulus.

55. A method according to claim 52 wherein said normalized waveform has one shape and distribution when said relevant specific information is detected in said subject, and a generally opposite shape and distribution when said relevant specific information is not detected in said subject.

56. A method according to claim 47 further comprising performing a function using a device actuated in response to detection of said information in said subject.

57. A method of detecting information stored in a brain of a subject comprising:
   presenting to said subject relevant and irrelevant stimuli;
   detecting an electrical brain response from said subject in response to each of said stimuli;
   analyzing said electrical brain responses for uncovering an electrically negative component thereof having an onset latency greater than about 800 msec and having a peak thereafter; and
   comparing said electrical brain responses due to said relevant and irrelevant stimuli for detecting said information in said subject brain based on said negative component.

* * * * *